United States Patent
Mendoza-Frohn et al.

[11] Patent Number: 5,510,499
[45] Date of Patent: Apr. 23, 1996

[54] PROCESS FOR THE ISOLATION OF PURIFIED ETHYLENE GLYCOL CARBONATE (EGC)

[75] Inventors: Christine Mendoza-Frohn, Erkrath; Paul Wagner, Düsseldorf; Hans-Peter Wirges, Krefeld, all of Germany

[73] Assignee: Bayer Aktiengesellschaft, Leverkusen, Germany

[21] Appl. No.: 276,748

[22] Filed: Jul. 18, 1994

[30] Foreign Application Priority Data

Jul. 26, 1993 [DE] Germany ............ 43 25 016.5

[51] Int. Cl.$^6$ .............................................. C07D 317/38
[52] U.S. Cl. ..................................................... 549/229
[58] Field of Search ............................................. 549/229

[56] References Cited

U.S. PATENT DOCUMENTS

| | | | |
|---|---|---|---|
| 2,766,258 | 10/1956 | Malkemus | 260/340.2 |
| 2,994,705 | 8/1961 | Crosby et al. | 260/340.2 |
| 3,025,305 | 3/1962 | Verdol | 260/340.2 |
| 3,621,664 | 11/1971 | Saxer | 62/58 |
| 4,314,945 | 2/1982 | McMullen et al. | 260/340.2 |
| 4,776,177 | 10/1988 | Jancic et al. | 62/123 |

FOREIGN PATENT DOCUMENTS

| | | |
|---|---|---|
| 0218545 | 4/1987 | European Pat. Off. . |
| 0521499 | 1/1993 | European Pat. Off. . |
| 1226117 | 10/1966 | Germany . |
| 1272932 | 7/1968 | Germany . |
| 2855232 | 6/1979 | Germany . |
| 1086028 | 10/1967 | United Kingdom . |

OTHER PUBLICATIONS

Weast, R. C. et al. *CRC Handbook of Chemistry and Physics* (CRC Pr., Boca Raton), p. F-298 (1982).

Sulzer, "Fraktionierte Kristallisation", cover page +pp. 2–12.

Industrial and Engineering Chemistry, vol. 50, No. 5, May 1958, pp. 767–770; "Preparation and Properties of the Alkylene Carbonates", W. J. Peppel publication month not provided.

Chem. Ing. Tech., vol. 57, No. 2, 1985, pp. 91–103; "Die Schmelzkristallisation von organischen stoffen und ihre . . . ", R. Sammet.

Chem. Ing. Tech., vol. 63, No. 9, 1991, pp. 881–891; "Schmelzkristallisation–theoretische voraussetzungen und . . . ", G. Wellinghoff et al.

Chemical Abstracts, vol. 118, 1993, p. 140; CA#171590b: "Method and apparatus for separation and . . . ", S. Ritner et al. Publication month not provided.

Chemical Abstracts, vol. 66, 1967, p. 2673, 23–Alipahtic Compounds; CA #28342z: "Purification by continuous crystallization . . . ", I. Ciolan et al. Publication month not provided.

Chemical Abstracts, vol. 66, 1967, p. 2679, 23–Aliphatic Compounds; CA #28389v: "Ethylene carbonate", H. J. Zimmer Verfahrenstechnik Publication month not provided.

*Primary Examiner*—Cecilia Tsang
*Assistant Examiner*—King Lit Wong
*Attorney, Agent, or Firm*—William C. Gerstenzang; Sprung Horn Kramer & Woods

[57] ABSTRACT

Ethylene glycol carbonate (EGC) can be isolated in purified form from contaminated material which contains impurities from the group comprising starting materials, by-products and/or catalysts of the preparation process in that the contaminated EGC is subjected to a fractional melt crystallization and the crystals of the purified EGC formed in this case are mechanically separated off from the remaining impurities dissolved in the residual melt.

7 Claims, No Drawings

PROCESS FOR THE ISOLATION OF PURIFIED ETHYLENE GLYCOL CARBONATE (EGC)

BACKGROUND OF THE INVENTION

1. Field of the Invention

The present invention relates to a process for the isolation of purified ethylene glycol carbonate (EGC) from a contaminated EGC which contains impurities from the group comprising starting materials, by-products and/or catalysts of the preparation process, in which the contaminated EGC is subjected to a fractional melt crystallization. The crystals of purified EGC formed in this case are then mechanically separated off from the remaining impurities dissolved in the residual melt. This novel isolation method is energy-saving and material-saving and does not require use of additives, for example solvents. As a result, particularly high degrees of purity of the EGC and the virtually complete reuse of the preparation catalyst are made possible.

2. Description of the Related Art

It is known that the EGC can be prepared by various routes, for example from ethylene glycol and phosgene (DE-AS (German Published Specification) 12 26 117), from ethylene oxide or ethylene chlorohydrin and carbon dioxide (Chem. Ing. Techn. 43 (1971), 903 ff.; Fette, Seifen, Anstrichmittel 73 (1971), 396 fl.; DE-OS (German Published Specification) 28 55 232, equivalent to U.S. Pat. No. 4,314,945; Ind. Eng. Chem. 50 (1958), 767–77.0) and from ethylene, oxygen and carbon dioxide (U.S. Pat. No. 3,025, 305). In these cases, the EGC generally arises in a form contaminated by the various substances from the preparation process. In the process starting from ethylene oxide and carbon dioxide, the crude product further contains the dissolved catalyst, for example quarternary ammonium compounds.

A number of purification processes for the EGC have therefore become known. Such a purification is carried out in the majority of cases by vacuum distillation. In this vacuum distillation, in the case of contamination of the EGC with the starting material or by-product glycol, an azeotropic mixture of glycol and EGC passes over the column head, while residual EGC is obtained at the column foot. If the crude EGC to be purified additionally contains a dissolved catalyst from the preparation process, this must be separated off before the vacuum distillation described for the removal of glycol from the crude product. Thus, for example, in the process described in Chem. Ing. Techn. and Fette, Seifen, Anstrichmittel (loc. cit.) two thin-film distillations are first carried out to separate off the catalyst. Most of this catalyst separated off can then be returned back to the preparation reaction to give EGC. In the thin-film evaporators, small amounts of by-products are simultaneously separated off. Only after these thin-film distillations is the above-described azeotropic distillation for the removal of glycol carried out and the EGC obtained at the column foot is fed to a further rectification. By means of this procedure, starting from a crude product containing 96–98% EGC according to gas-chromatographic analysis, a pure product is achieved containing 99.5% EGC, and further containing 0.025% water and 0.1% glycol (again according to gas-chromatographic analysis).

Distillation processes for the purification of EGC generally have the disadvantage that a vacuum distillation system must be operated at pressures of at most 50 mbar, since, at higher pressures, which simultaneously correspond to higher distillation temperatures, the EGC is already partially decomposed and thus a reduction of the yield must be expected. This risk of the decomposition of the EGC is present in particular when the crude product still contains, in dissolved form, the catalyst from the reaction, for example of ethylene oxide with carbon dioxide, and this catalyst is likewise separated off by distillation before the fine purification by distillation. Thus, for example, in Ind. Eng. Chem. (loc. cit.) it is described that the pressure mentioned of at most 50 mbar is advisable in order to ensure a good product quality. However, since the catalyst is concentrated in the distillation bottoms by distilling off the pure EGC and, on the other hand, the degree of decomposition of the EGC depends strongly on the concentration of the catalyst dissolved therein, according to the said publication, at an input concentration of 0.25 to 0.5% by weight of catalyst, no more than 90 to 95% of the EGC must be distilled off. A further risk is that the catalyst itself can be decomposed during this distillation operation. If it is thus desired to return the distillation bottoms, which represent a concentrated catalyst solution, to the preparation reaction, a portion of the catalyst must be discarded and replaced by new catalyst. In the said publication, for example, replacement of 30% of the catalyst solution is recommended.

It is further known to purify EGC by extraction with solvents. In this case, a solvent mixture, a single solvent, such as ethylene dichloride, methylene dichloride or chloroform, or a hydrocarbon together with water (to receive the water-soluble catalyst) can be used (U.S. Pat. No. 2,766, 258). In this case a degree of purity of 99.1% EGC is achieved. The disadvantage of an extraction process is the necessary subsequent separation by distillation of the EGC from the extraction solvent. In the case of catalyst-laden crude products, there is additionally the risk during the extraction that residues of the solvent used for the extraction pass into the reaction circulation during the return of catalyst where they can lead to by-products and decomposition reactions.

It has also already been attempted to purify EGC by recrystallization from a solvent, for example from toluene (U.S. Pat. No. 2,994,705). The disadvantage of such a process is that, to achieve a sufficient purity, repeated recrystallization is necessary. A further disadvantage, which becomes conspicuous in a corresponding manner and as in the extraction, is the necessity of the separation of any catalyst present from the recrystallization solvent.

In a still further method for the purification of crude EGC, this is crystallized in a continuous manner in counter-current from ethylene glycol as solvent (DE-AS (German Published Specification) 12 72 932). In this case, a preheated EGC solution is cooled in the upper part of a crystallization column until the formation of EGC crystals, while the lower part of the column is kept at a temperature of 40° to 50° C. The heating and cooling are coordinated with each other in such a way that a downwards directed crystal flow results; the purified EGC is taken off in the molten state at the column bottom, and the exhausted mother liquor is taken off at the upper part of the column. The crystalline state of the EGC in this purification process is only a briefly occurring intermediate step. By this process, purities of 99.67% EGC (according to gas-chromatographic analysis) are achieved, if the procedure starts from a reaction mixture which arises in the preparation of EGC from ethylene glycol and phosgene. In addition to EGC and glycol, ethylene chlorohydrin and hydrochloric acid are further present in these reaction mixtures. These contents in the crude product are not considered in DE-AS (German Published Specification) '932 itself;

however, these can be inferred from Rev. Chim. (Bucharest) 17 (1966), 482–485 where the process described in DE-AS (German Published Specification) '932 is worked out in more detail. If, according to this, mixtures of 50 to 60% EGC, 30 to 40% ethylene glycol, 1% hydrochloric acid, 4 to 5% ethylene chlorohydrin and 5% water are used, a purified EGC arises having the following values: 96.4–98.3% EGC, 0.65–1.41% ethylene glycol, 0.14–0.28% ethylene chlorohydrin and 0.19–0.39% water. However, a purified EGC is thus present whose very high residues of ethylene glycol, ethylene chlorohydrin and, in particular, water can lead in the further use of the EGC to its decomposition and to side reactions.

In a counter-current crystallization from ethylene glycol as that described, in the case of catalyst-laden crude EGC, the catalyst after the crystallization would be present together with the minor components dissolved in the ethylene glycol. If it is desired to return the catalyst to the preparation reaction, a step to separate the catalyst from the ethylene glycol would have to be carried out, since the ethylene glycol, in the presence of the catalysts used and the operating conditions to be maintained in this case, would lead to side reactions of the ethylene oxide. This represents an extremely disadvantageous burden of such a crystallization.

It was therefore desirable to have available a purification process for contaminated EGC which is energy-saving and material-saving, which leads neither to decomposition of the EGC itself nor of the catalyst and, moreover, is to be operated without additives, such as solvents for extraction or crystallization.

SUMMARY OF THE INVENTION

It has now surprisingly been found that, in the fractional crystallization of EGC from the melt, that is without addition of solvents, high purities of the EGC are obtained. Both the impurities from the crude EGC and any catalysts originating from the preparation process and dissolved in the crude EGC are incorporated in the crystals only to an extremely low extent.

A further advantageous finding of the melt crystallization according to the invention is the particularly gentle treatment in this case of the catalyst which remains in the melt and therefore can generally be completely returned to the reaction for the preparation of the EGC. A further advantage is the high crystallization temperature of about 37° C. and the possibility associated therewith of being able to conduct away cheaply the heat of crystallization even at summer temperatures by secondary cooling circulation water available even at an admission temperature of 29°– 30° C. In comparison with distillation processes, it is further advantageous that the heat of crystallization of the EGC is only about one third of its heat of evaporation.

A process has been found for the isolation of purified ethylene glycol carbonate (EGC) from a contaminated EGC which contains impurities from the group comprising starting materials, by-products and/or catalysts of the preparation process, which is characterized in that the contaminated EGC is subjected to a fractional melt crystallization and the crystals of the purified EGC formed in this case are mechanically separated off from the remaining impurities dissolved in the residual melt.

DETAILED DESCRIPTION OF THE INVENTION

The contaminated EGC to be used according to the invention is both a prepurified EGC, which is to be subjected to a further fine purification stage, and also a crude reaction mixture which originates directly from the preparation of EGC. Because of the simplicity of the process according to the invention, one will dispense in many cases with first subjecting EGC to a different purification in order then to apply the purification process according to the invention; it is therefore preferred, as contaminated EGC, to treat directly in the manner according to the invention a reaction mixture from the preparation of EGC. Because of the above-described gentle removal of a catalyst, it is further preferred to use according to the invention those preparation mixtures of EGC which originate from a catalysed preparation process.

The process according to the invention of the fractional melt crystallization of contaminated EGC can be carried out both discontinuously and continuously; it is preferably carried out discontinuously.

For the purification according to the invention of EGC or separating off EGC from crude products which may contain catalyst, crystallization processes can be used, such as are described, for example, in Chem. Ing. Techn. 57 (1985), 91; Chem. Ing. Techn. 63 (1991), 881 or in the brochure of the Sulzer company on fractional crystallization of August 1992. In this case, these are, for example, processes with the formation of coherent crystal layers which are frequently operated in cycles, tube-bundle crystallizers or modified plate heat exchangers of diverse construction being used with or without pumped circulation of the melt, with and without use of pulses and/or with and without subdividing the tubes into segments having a separate delivery. Furthermore, falling-film crystallizers of diverse type are useful with and without internals for improving the heat transfer, as are described, for example, in EP 218 545. Other apparatuses which can be used are bubble column crystallizers, crystallizer rolls and crystallizer belts.

A further continuously operating crystallization device with formation of coherent crystal layers having a circulating transport device, with devices for feeding the melt and for conveying away the purified product and devices for sweating the crystals are described in EP 521 499.

Melt crystallization processes known to those skilled in the art further include the processes having formation of crystal suspensions which are separated into solid and residual melt in a further process step, generally by a mechanical liquid separation. These predominantly continuously operated processes are carried out, for example, in agitated-tank crystallizers with and without external circulation, in scraped-surface coolers of diverse construction with or without cascading, in disc crystallizers or static crystallizers of various designs and in crystallization columns, which either are constructed as pressure columns, in which the transport of crystals and melt is effected externally by pumps or ram presses, or as a column having mechanical forced transport devices, such as special stirrers, screws, helices or spirals. These crystallization columns can also be operated in counter-current mode.

For the process according to the invention, tube-bundle crystallizers, plate heat exchangers of diverse construction with and without pump circulation of the melt or falling-film crystallizers are preferably used.

The crystallization operation in the process according to the invention for the purification of an already prepurified EGC or for separating off EGC from the reaction solution, which may contain catalyst, from the preparation can be initiated both by spontaneous nucleation and by defined supply of crystallization nuclei (seeding). Both forms are known in their fundamental applicability. Because of the more highly pronounced reproducibility, the initiation of crystal formation by seed crystals is preferred.

Not only procedures with the formation of coherent crystal layers but also those with formation of crystal suspensions, which can both be carried out in the process according to the invention, can be operated in multiple stages in order to achieve the target product purity or the required yield of pure product. This can be necessary, for example, if one starts from a particularly contaminated crude EGC and/or sets particularly high purity requirements for the pure EGC. The individual stages can be carried out in a plurality of sequential system components or, staggered in time, in the same crystallizer.

The process according to the invention for the isolation of purified EGC by melt crystallization can be joined to purification processes by distillation. It is thus possible, before employment of the melt crystallization, in particular in separating off EGC from reaction solutions which may contain catalyst, to perform in advance a gentle distillation of readily volatile reaction products and only then to subject the remaining distillation bottoms to the melt crystallization according to the invention. Such a gentle advance distillation, for example under reduced pressure and with application of a preset maximum temperature, is in accord with the melt crystallization according to the invention which is gentle to the product.

The combination of the process according to the invention with separation layers by distillation likewise leads to high degrees of purity of the EGC isolated in this case and to only a low degree of decomposition of EGC and catalyst during such a combined purification and separation step. For example, from a catalyst-containing crude product, the catalyst can first be separated off from the melt in an optionally multiple-stage crystallization, a small residue of catalyst remaining in the crystals, depending on the type of melt crystallization process selected, depending on the choice of the parameters to be employed, such as temperatures, cooling and heating rates etc. and depending on the number of the process stages. These traces of catalyst, in a subsequent, mild distillation in vacuo, only lead to EGC decompositions to a far lesser extent than is the case in the distillation of the crude product in the presence of the entire amount of catalyst. An additional advantage of such a combined process procedure, in comparison with a process purely by distillation, results in a virtually complete recyclability of the catalyst to the reactor for the preparation of EGC, which can be restricted only by conditions of the EGC preparation process.

Pure EGC has a melting point of 36.4° C. The temperature range for the process inevitably resulting from this extends through the region from 45° C. down to 0° C.

When the process according to the invention is carried out in tube-bundle crystallizers or plate heat exchangers, the melt to be purified is cooled in the range 38°–20° C., preferably 37°–25° C., at a cooling rate of the cooling medium of 40–0.1 K/h, preferably 10–0.5 K/h; during this cooling phase, the crystallization operation is initiated by spontaneous nucleation or by defined supply of nuclei (seeding), preferably by seeding. At the lowest temperature of the cooling medium, before separating off the residual melt, a holding time of up to 100 minutes can be maintained, however, if appropriate, this holding time can be dispensed with. The holding time, taking into consideration both variants, is therefore 0 to 100 minutes, preferably 1 to 70 minutes. After this the residual melt is separated off and the crystals are further purified by so-called "sweating" at a heating rate of the heating medium of 40 to 0.1 K/h, preferably 20 to 0.5 K/h, up to a final temperature of 22° to 37° C., preferably 28° to 36° C.

The relationships described for steady-state crystallization processes using tube bundles or plate heat exchangers also apply in principle in the same manner to the procedure in falling-film crystallizers; however, in addition, still other relationships, such as for example the specific pipe loading by the melt and the local temperature difference between melt and heating medium, must also be taken into account for their effect on the purity of the crystals. However, these relationships are known in principle to those skilled in the art.

The EGC crude products which are usable in the process according to the invention can contain the proportions of impurities, by-products, residual starting materials and catalysts which are known to those skilled in the art from the various preparation processes for EGC. The possibility already mentioned of carrying out the process according to the invention in multiple stages can take into account different levels of the impurities mentioned. Examples of impurities present which can be mentioned by way of example from the EGC preparation process from ethylene oxide and $CO_2$ in the presence of catalysts are: the catalysts; products from the rearrangement of ethylene oxide to give acetaldehyde and polycondensation thereof, such as linear and cyclic, possibly polyunsaturated, aldehydes; glycol and linear or cyclic products from the condensation thereof; products from the reaction of ethylene oxide with glycol or acetaldehyde under the influence of the catalyst present.

Catalysts from the RGC preparation process which can be removed as impurity in the context of the process according to the invention are virtually all previously proposed catalysts. These are, for example: alkali (ne earth) metal bromides and iodides, guanidines and hydrobromides or hydroiodides thereof, tetraalkylammonium bromides and tetraalkylammonium iodides, phosphonium bromides and phosphonium iodides, pyridinium halides, sulphonium, stibonium and arsonium halides, zinc halides and lead halides, alkyltin compounds or mixtures of alkali metal halides with halides of divalent metal ions. These catalysts are known to those skilled in the art from numerous publications. The following catalysts, which can be present as impurities to be removed, can be referred to in particular: alkali metal bromides and alkali metal iodides, tetraalkylammonium bromides and tetraalkylammonium iodides, phosphonium halides, guanidinium halides and mixtures of alkali metal halides with halides of divalent metals.

EXAMPLES 1 TO 8

The data listed in Tables 1 and 2 for Examples 1 to 6 for the purification of EGC and/or for separating off EGC from catalyst-containing crude products were obtained in a tube-bundle crystallizer (tube diameter 4 cm), and the data for examples 7 and 8 were obtained in a falling-film crystallizer (tube diameter 4.9 cm; height 1.2 m). The examples 1–6 were carried out with defined supply of nuclei (seeding).

Table 1 contains, for the six in a tube-bundle crystallizer carried out examples, the figures for the starting and final temperature of the cooling phase, for the seeding temperature, cooling rate of the cooling medium, holding time, heating rate of the heating medium and the degree of the crystals/melt separation. In the falling-film crystallizer was worked at a constant crystallization temperature; no seeding was applied. The velocity of metering the educt to be purified in examples 7 and 8 was set to 30 g/min.

The analytical results for the eight examples are listed in Table 2.

Composition of the crude product, the crystals and the residual melt were determined with the aid of a gas chromatograph. The Hazen colour index, which quantifies the yellow tinge in the EGC samples due to the polycondensed aldehydes, can be considered as a further, highly sensitive measure of the purity of crude product, crystals and melt. The catalyst concentrations in crude product, crystals and melt were determined in the case of the inorganic salts with the aid of atomic absorption spectroscopy, in the case of the ammonium halides via analysis of the halide by argentometric titration.

The EXAMPLES 1 to 6 verify that, even with a single-stage tube-bundle crystallization, high purities of the EGC and low inclusion rates of the catalyst in the crystals can be achieved. In the case of the EGC separation from catalyst-containing crude products, in which the catalyst-containing melt is returned to the preparation process, because of the gentle separation method, these melts are also not additionally thermally stressed and therefore equally show a high purity.

EXAMPLES 1 and 2 verify the influence of the concentration of impurities in the crude EGC on the quality of the pure EGC: impurities, such as glycol and polycondensed aldehydes, are scarcely included in the crystals and collect preferentially in the melt. Despite the highly differing colour indices of the crude products in the two examples, the crystals in both cases have a colour index of 10 (colourless). In the case of glycol, a somewhat elevated inclusion into the crystals at relatively high concentration in the crude product is observed (EXAMPLE 1).

EXAMPLE 4, in comparison to EXAMPLE 3, shows that a higher catalyst concentration in the crude product under otherwise identical conditions leads to a slightly higher rate of inclusion of the catalyst in the crystals. The catalyst concentration in the crystals is, at 0.03 to 0.04%, very low for a single-stage crystallization. The rate of inclusion of the catalyst is further dependent on the type of catalyst, as the comparison of EXAMPLES 4, 5 and 6 verifies. However, with all catalysts, a marked concentration in the melt can be recorded.

EXAMPLES 7 and 8 demonstrate that by carrying out the purification of the EGC in a falling-film crystallizer, at the same ratio crystals/melt, even higher rates of separation of catalysts and by-products can be achieved, compared with the static performance in the tube-bundle crystallizer, i.e. a higher quality of the purified EGC can be obtained.

TABLE 1

Test Conditions for Examples 1 to 8

| No. | Starting temp. | Seeding temp. (°C.) | Final cooling temp. (°C.) | Cooling rate Cooling medium (K/h) | Holding time (min) | Heating rate Heating medium (K/h) | Crystals/melt |
| --- | --- | --- | --- | --- | --- | --- | --- |
| 1* | 35.9 | 35.1 | 29.9 | 2.2 | 0 | 2.4 | 1:1 |
| 2* | 36.0 | 35.4 | 30.0 | 2.2 | 0 | 2.4 | 1:1 |
| 3* | 35.9 | 35.1 | 29.9 | 2.2 | 0 | 2.4 | 1:1 |
| 4* | 36.0 | 35.4 | 30.0 | 2.2 | 0 | 2.4 | 1:1 |
| 5* | 36.6 | 35.9 | 30.6 | 2.4 | 20 | 2.4 | 1:1 |
| 6* | 36.5 | 35.9 | 31.2 | 2.4 | 15 | 2.4 | 1:1 |
| 7** | 35.0 | — | — | — | — | 2 | 1:1 |
| 8** | 35.0 | — | — | — | — | 2 | 1:1 |

\* = static crystallization in a tube-bundle crystallizer
\*\* = falling-film crystallization (constant crystallization temperature; educt feed = 30 g/min)

TABLE 2

Results for Examples 1 to 8 (Expl. 1 to 6 = static crystallization in a tube-bundle crystallizer; Expl. 7 and 8: falling-film crystallizer)

| | Crude product | | | Crystals | | | Melt | | |
| --- | --- | --- | --- | --- | --- | --- | --- | --- | --- |
| No. | GC-Analysis (%) | Hazen colour index | Catalyst content (% by weight) | GC-Analysis (%) | Hazen Colour index | Catalyst content (% by weight) | GC-Analysis (% by weight) | Hazen colour index | Catalyst content (% by weight) |
| 1 | 98.84 EGC 0.93 Glycol | 20–30 | — | 99.74 0.21 | 10 | — | 98.10 1.51 | 40 | — |
| 2 | 99.40 EGC 0.39 Glycol | 60 | — | 99.92 0.05 | 10 | — | 98.92 0.70 | 80 | — |
| 3 | 98.84 EGC 0.39 Glycol | 20–30 | 0.08 NaBr/ZnBr$_2$ | 99.73 0.24 | 10 | 0.03 | 98.10 1.51 | 40 | 0.20 |
| 4 | 99.40 EGC 0.39 Glycol | 60 | 0.35 NaBr/ZnBr$_2$ | 99.91 0.05 | 10 | 0.04 | 98.92 0.70 | 80 | 0.66 |
| 5 | 99.77 EGC 0.16 Glycol | 30–40 | 0.4 Bu$_4$NBr | 99.86 0.11 | 10 | 0.03 | 99.63 0.26 | 70 | 0.60 |
| 6 | 99.75 EGC 0.18 Glycol | 30–40 | 0.26 Et$_4$NBr | 99.85 0.13 | 10 | 0.01 | 99.64 0.26 | 70 | 0.53 |
| 7 | 99.8 EGC 0.2% Glycol | 30 | 0.15 NaBr/ZnBr$_2$ | 99.9% EGC <0.1% Glycol | 0 | 0.002 | 99.6 0.3 | 90 | 0.29 |
| 8 | 99.8% EGC | 30 | 0.30 | 99.9 EGC | 0 | 0.007 | 99.6 | 90 | 0.61 |

TABLE 2-continued

Results for Examples 1 to 8 (Expl. 1 to 6 = static crystallization in a tube-bundle crystallizer; Expl. 7 and 8: falling-film crystallizer)

| | Crude product | | | Crystals | | | Melt | | |
|---|---|---|---|---|---|---|---|---|---|
| No. | GC-Analysis (%) | Hazen colour index | Catalyst content (% by weight) | GC-Analysis (%) | Hazen Colour index | Catalyst content (% by weight) | GC-Analysis (% by weight) | Hazen colour index | Catalyst content (% by weight) |
| | 0.2% Glycol | | NaBr/ZnBr$_2$ | <0.1% Glycol | | | 0.3 | | |

EGC = Ethylene glycol carbonate, Bu$_4$NBr = Tetrabutyl-ammonium bromide; Et$_4$NBr = Tetraethyl-ammonium bromide
*) without catalyst; remainder to 100% corresponds to polycondensed aldehydes, diglycol, triglycol

What is claimed is:

1. A process for the isolation of purified ethylene glycol carbonate (EGC) from a contaminated EGC which contains impurities from the group comprising starting materials, by-products and/or catalysts of the preparation process, wherein the contaminated EGC is subjected to a fractional melt crystallization wherein the melt of the EGC to be purified is cooled in range from 38° to 20° C. at a cooling rate of the cooling medium of 40 to 0.1 K/h and is carried out with the aid of a tube-bundle crystallizer, plate heat exchanger or a falling-film crystallizer and the crystals of the purified EGC formed in this case are mechanically separated off from the remaining impurities dissolved in the residual melt.

2. The process of claim 1, wherein the melt is cooled in the range from 37° to 25° C.

3. The process of claim 1, wherein the cooling rate is 10 to 0.5 K/h.

4. The process of claim 1, wherein, after a holding time of 0 to 100 minutes at the lowest temperature point of the cooling medium, the residual melt is separated off and the crystals are further purified by sweating at a heating rate of the heating medium of 40 to 0.1 K/h up to a temperature of 22° to 37° C.

5. The process of claim 4, wherein the holding time is 1 to 70 minutes.

6. The process of claim 4, wherein sweating is carried out at a heating rate of 20 to 0.5 K/h.

7. The process of claim 4, wherein sweating is carried out up to a temperature of 28° to 36° C.

* * * * *